United States Patent [19]
Bouwens et al.

[11] Patent Number: 5,879,730
[45] Date of Patent: *Mar. 9, 1999

[54] METHOD OF ENHANCING COLOR IN A TEA-BASED FOODSTUFF

[75] Inventors: Elisabeth Cornelia Bouwens, Breda, Netherlands; Ketan Trivedi, Bangalore, India; Cornelis van Vliet, Hardinxveld-Giessendam; Cornelis Winkel, Massluis, both of Netherlands

[73] Assignee: Lipton, Division of Conoco Inc., Engelwood Cliffs, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 810,036

[22] Filed: Mar. 4, 1997

[51] Int. Cl.$^6$ ........................................................ A23B 7/10
[52] U.S. Cl. ............................... 426/52; 426/49; 426/262; 426/270; 426/597
[58] Field of Search ................................ 426/49, 52, 590, 426/597, 250, 262, 263, 270

[56] References Cited

U.S. PATENT DOCUMENTS

| | | | |
|---|---|---|---|
| 3,812,266 | 5/1974 | Sanderson et al. | 426/52 |
| 4,051,264 | 9/1977 | Sanderson et al. | 426/52 |
| 5,445,836 | 8/1995 | Agbo et al. | 426/52 |

OTHER PUBLICATIONS

Patent Abstracts of Japan, Abstracting JP 57–206391, Dec. 1982.

*Primary Examiner*—Leslie Wong
*Attorney, Agent, or Firm*—James J. Farrell

[57] ABSTRACT

A method of inducing the formation of color determining compounds in a tea-based food product, characterized in that the tea leaves are treated with an exogenous laccase, polyphenol oxidase or peroxidase, in combination with a pretreatment with a tannase. Also, a treatment with a fungal laccase form a Pleurotus species can be performed to enhance the color of a tea-based product.

8 Claims, No Drawings

METHOD OF ENHANCING COLOR IN A TEA-BASED FOODSTUFF

The present invention relates to a method of inducing the formation of coloured compounds in a tea-based product. More specifically, the invention involves using known exogenous oxidising enzymes to brighten or intensify the colour of tea.

Colour can be one of the most important factors affecting a consumer's decision to choose one product over another. Apart from the visual impact, it can influence one's perception of the product's taste and quality.

This can be especially true for tea-based beverages. Whether freshly brewed, taken with or without milk, instant or ready-to-drink, tea can be enjoyed or dismissed by consumers before the first sip.

Black tea is traditionally produced by oxidising and drying freshly plucked green tea leaves. The harvested leaves are usually the so-called flush or new growth comprising the apical bud and several new leaves below it (typically two leaves and a bud). The oxidation step involves converting the colourless catechins in the leaves to a complex mixture of yellow and orange to dark-brown substances and producing a large number of aromatic volatile compounds.

The colourful oxidation products include theaflavins and thearubigins. Theaflavins comprise several well-defined catechin condensation products that are characterised by their benztropolone ring. Thearubigins are a group of undefined molecules with a large variance in molecular weight. They have a large variety of colours ranging from yellow to dark red and brown.

It is well known to use exogenous enzymes such as tannases and cellulases to increase the yield of tea liquor from tea leaves. It is also known to use polyphenol oxidases (PPO's) in producing tea-like colours.

JP-A-49-4394 (CA 1974: 81, 103275v) discloses fermentation of tea leaves with PPO's from *Alternaria tenuis* or Cladosporium species, resulting in the production of black tea.

Similarly, the use of *Alternaria tenuis* PPO was reported to shorten the fermentation time and to increase the colour of black tea (Kato et al, CA 1987: 107, 11452g) and to darken cocoa, coffee and tea extracts (Motoda, Nippon Shokuhin Kogyo Gakkaishi 1982, 1, 11–5).

JP-A-57-206391 (=JP-B-5393) discloses the production of flavonoid pigments by treating plant tissue, such as green tea, with a tyrosinase or *Alternaria tenuis* PPO. Li and Guo (Linchan Huaxue Yu Gongye, 1988, 8, 33–38) describe the catalytic oxidation of green tea tannin by immobilised laccases and native laccases from plant origin (*Rhus verniclfera*).

The use of enzymes in the manufacture of black tea and instant tea was reviewed by Sanderson and Coggon (ACS Symposium Series 1977, 81, 12–26). The enzymes include catechol oxidase for black tea production and tannase and PPO for instant tea production. No laccases are mentioned.

The present inventors have found that the combined use of particular enzymes, i.e. a treatment with one or more exogenous peroxidases, polyphenol oxidases and/or laccases preceded by or simultaneously with one or more tannases, results in a surprising improvement of the colour of the tea-based product. It was also found that a particular group of laccases, i.e. fungal laccases, especially from a Pleurotus species, when used alone, also leads to an unexpectedly enhanced colour.

Accordingly the present invention in a first aspect relates to a method of enhancing the colour in a tea-based food product, like liquid tea or dry instant tea, wherein tea leaves or tea extracts are subjected to at least one oxidizing enzyme selected from exogenous peroxidases, laccases and polyphenol oxidases and at least one tannase. In another aspect, the invention relates to such a method wherein tea leaves or tea extracts are oxidised in the presence of at least one fungal laccase, especially from a species of the genus Pleurotus, in particular *Pleurotus ostreatus*.

The present inventors have found that using enzymes or enzyme combinations in this way can optimise the intensity of the colour of a tea extract and/or increase the theaflavin content. This results in a more desirable product.

Peroxidases (EC 1.11.1.1–1.11.1.11) that can be used according to the invention include the haemoprotein peroxidases (EC 1.11.1.5–1.11.1.8) and the non-haemoprotein peroxidases such as haloperoxidases. Preference is given to peroxidases which are cofactor-independent, in particular to the classical peroxidases (EC 1,11.1.7). Peroxidases can be derived from any source, including plants, bacteria, filamentous and other fungi and yeasts. Examples are horseradish peroxidase, soy-hull peroxidase, Arthromyces and Coprinus peroxidases. Several peroxidases are commercially available. The peroxidases require hydrogen peroxide as an electron acceptor.

Polyphenol oxidases (EC 1.10.3.1) include tyrosinases and catechol oxidases. Their systematic name is 1,2-benzenediol: oxygen oxidoreductase, other names include o-diphenol oxidase, diphenol oxidase, o-diphenolase and phenolase.

Suitable polyphenol oxidases may be obtained from fungi such as Chaetomium, Phlebia, Strepotmyces, Pleurotus, Lentinus, Flammulina, Phanerochaete, Symbiobacterium, or Agaricus; plants such as apple, pear, avocado, strawberry, peach, potato, grape, tomato, broad bean, banana, fig, artichoke, cacao, egg plant and kiwifruit; and animals such as lobster and frog. The polyphenol oxidases require oxygen as an electron acceptor.

Laccases (EC 1.10.3.2) are sometimes referred to as p-diphenol oxidases. However, this name is too restricted since their substrate specificity is much broader. While they are sometimes grouped under the polyphenol oxidases (PPO's), laccases can be discriminated from other PPO's like tyrosinases and catechol oxidases by the fact that they contain at least three copper ions per molecule/subunit (aminoacid chain). Tyrosinase and catechol oxidase contain 1 or 2 copper ions. The enzyme urishol oxidase is also considered to be a laccase. Their natural function is not well understood but it has been suggested that they play a role in the mineralisation of lignin. The laccases also require oxygen as an electron acceptor.

Laccases can also be distinguished from other PPO's on the basis of their activity range. Laccase can oxidise hydroquinones, whereas other PPO's cannot. The preferred laccases show good activity towards syringaldazine (more than 100 U/mg protein; 1 unit (U) is defined as 1 nmole/s= 1nkatal) and catechin (more than 1,500 AU/mg protein, wherein 1 AU is defined as 0.001 $\Delta A_{450}$), while the other PPO's are less active with these substrates. The syringaldazine assay is performed as follows: 50 $\mu$l of enzyme solution is added to a mixture of 1200 $\mu$l 25 mM sodium acetate, pH 5.5, 250 $\mu$l 1 g/l polyethylene glycol (PEG 8000) in Milli Q water and 500 $\mu$l 800 $\mu$M syringaldazine solution in methanol; $\Delta A_{530}$/min between t=60 s and t=120 s is measured at 30° C.; $\epsilon$=104 mM$^{-1}$.cm$^{-1}$. pathlength in cuvette=1 cm. The catechin assay is performed as follows: 50 $\mu$l of enzyme solution is mixed with 0.2M catechin dissolved in oxygen-free ethanol and 900 $\mu$l of air-sturated McIlvain buffer pH=6. $\Delta A_{400}$ is measured. Also, the preferred laccases are not seriously inhibited by 1 mM 4-hexylresorcinol or salicylhydroxamic acid, whereas catechol oxidases are inhibited by these agents. The preferred laccase has a redox potential of more than 550 mV.

Laccases can be derived from plant sources such as Rhus, Daucus, Iris, Rosmarinus, Solanum, or Vinca species or aleurone layer of grains. Preferably, laccases from microbial, especially fungal, sources such as Agaricus, Armillaria, Aepergillus, Basidiomycete PM1, Botrytis, Cerrena, Coriolus (=Polyporus=Tramete.), Cryptococcus, Curvularia, Daedalea, Flammulina, Ganoderma, Lentinus, Monocillium, Neurospora, Phlebia, Pletrotus, Pycnoporus, Rhizoctonia, Schizophyllum and Trichoderma are used.

Preference is given in particular to laccases derived from basidiomycetes (mushrooms with a stem) and/or white-rot fungi. Most preferred laccase is derived from food-grade mushrooms, such as Pleurotus species, in particular *P. ostreatus*, an edible basidiomycete having white-rot fungal properties.

Tannases (systematic name: tannin acylhydrolase, EC 3.1.1.20) hydrolyse gallate groups from tannin-like compounds including tea compounds. Suitable tannases, to be used in combination with a peroxidase, polyphenol oxidase or laccase, are exogenous, and can be derived e.g. from yeasts such as Candida species, or from fungi such as Aspergillus species.

For each of the enzymes described above, preference is given to enzymes derived from organisms which are acceptable for food purposes, i.e. which are food-grade.

The above-mentioned enzymes can also be obtained from genetically modified organisms. This would be the case when an enzyme-encoding gene of one of the organisms mentioned is transferred and expressed in another organism. Known examples include the production of *Phlebia radiata* laccase in *Trichoderma reesei* (M. Saloheimo et al in Bio/Technology 9, 987 (1991)), *Polyporus sintinus* laccase in *Aspergillus oryzae* (D. S. Yaver et al, Gentics and cellular biology of basidiomycetes III, Congress abstracts, London, C. F. Thurston and D. A. Wood, 16–19 June 1995) and *Myceliophthora thermophila* or *Scytalidium thermophilum* laccase in *A. oryzae* (WO 95/33836, WO 95/33837). Preferred host organisms are food-grade microorganisms, in particular yeast species, such as *Saccharomyces cerevisiae, Pichia pastorais* and *Hansenula polymorpha*, and fungal species such as Aspergillus sp., e.g. *A. oryzae* or *A. awamori*.

For the purposes of the present invention suitable enzyme concentrations range between about 0.0001 and about 2.5% on the basis of soluble tea solids, preferably between 0.001 and 0.3% (dry enzyme weight). Soluble tea solids are determined by filtering, drying and weighing. These concentrations apply both to the tannase as to the oxidising enzymes. The tannase treatment can be performed simultaneously with the treatment with oxidising enzyme, but preferably the tannase treatment is a pretreatment, which can be carried out simultaneously with the "fermentation" of the tea leaves, if appropriate.

The laccase treatment can be performed using tea leaves, i.e. green tea leaves or black tea leaves, preferably in the presence of water. The treatment can also be performed using green tea or black tea extracts, either direct extracts, or reconstituted extracts, i.e. redissolved dry extracted tea components. Furthermore, the laccase can be added to a conventional black tea "fermentation", i.e. during the primary oxidation of the green tea.

The preferred pH during the enzymatically catalysed oxidation is between pH 3 and pH 8, especially between pH 4 and pH 7. Suitable oxidation temperatures range from 10° to 70° C., the best temperatures being between 20° and 65° C. Suitable oxidation times depend on the temperature and the enzyme strength, and can be e.g. from 1 minute to 6 hours, in particular from 5 minutes to 3 hours. The enzyme may be removed afterwards e.g. by means of filtration, but in general removal of the enzyme is not necessary.

For the additional tannase pretreatment, similar conditions as for the peroxidase or laccase treatment can be used, i.e. a temperature of 10°–70° C., a pH from 3 to 8, and a concentration of between 0.0001 and 1 wt.%, in particular 0.0005 to 0.1 wt.%, on the basis of soluble tea solids. The presence of oxygen during tannase pretreatment can be excluded or not, or oxygen can be excluded during a first stage, followed by oxygen supply in a second stage before addition of peroxidase, laccase or polyphenol oxidase. As an alternative, a tannase treatment may be performed simultaneously with the peroxidase/laccase/polyphenol oxidase treatment, preferably with at least partial presence of hydrogen peroxide (in case of peroxidase) or oxygen (in case of laccase or polyphenol oxidase).

According to a particular embodiment of the invention, the enzymes are not added in soluble form, but are immobilised on a solid support. This applies both to the tannase and to the oxidising enzyme. The solid support can be a conventional resin e.g. packed in a column. The solid support can also be formed by beads, filters, and the like, made from polyacrylamnide, polysaccharides, polyamides or other insoluble organic or inorganic polymers.

The method of the invention can be used to produce tea-like beverages as such or to produce dry tea material such as soluble powders ("instant tea" and the like), which can be reconstituted to form tea-like beverages, or also to produce other edible products wherein a tea-like colour is desirable.

The method of the invention will now be described with reference to the following examples.

EXAMPLES

In the Examples 1 to 5 colour was measured using the CIE (Commission Internationale d'Eclairage) scale on a Hunter Lab DP 1000 or a standard spectrophotometer with appropriate software. The colour was measured using a sample path length of 1 cm. Measurements were performed at a concentration of 0.15% soluble tea solids and at pH 4, unless stated otherwise. The colour was analysed by means of parameters L* (0=black, 100=colourless), a* (negative= green, positive=red) and b* (negative=blue, positive= yellow). Control values refer to the colour before treatment.

Example 1

Fifty ml of a 0.1M McIlvain buffer (pH=6) containing 30 mg/l of laccase obtained from *Pleurotus ostreatus* and 35 g/l of instant green tea (Ceytea, Sri Lanka) were stirred at room temperature with air sparging. After 30 min, 0.2 g/l theaflavins had been formed as determined by HPLC. After 90 min. the colour was measured as shown in Table 1 below.

TABLE 1

|  | L* | a* | b* |
| --- | --- | --- | --- |
| Control before treatment | 98 | −3 | 12 |
| + air sparging | 97 | −1 | 1 |
| + air sparging + laccase | 84 | 7 | 87 |

These results demonstrate that laccase induces the formation of black tea-like colour determining compounds including theaflavins in a green tea based beverage.

Example 2

Fifty ml of a 0.1M McIlvain buffer (pH=6) containing 3 mg/l of laccase obtained from *Pleurotus ostreatus* and 30 g/l of instant black tea (Lipton, U.S.A.) were stirred at room temperature with air sparging. After 90 min. the colour was measured as shown in Table 2 below.

TABLE 2

|  | L* | a* | b* |
|---|---|---|---|
| Control before treatment | 90 | −4 | 39 |
| + air sparging | 91 | −5 | 39 |
| + air sparging + laccase | 77 | 8 | 17 |

These results demonstrate that laccase darkens an extract of black tea.

Example 3

A black tea extract (3% soluble solids) was treated with 0.5% laccase (weight % based on tea solids) from *Rigidoporus zonalis* (Takara, Japan) for 30 min at 50° C. under air sparging in 50 ml of McIlvain buffer (pH=6). After 30 min. the colour was measured as shown in Table 3.

TABLE 3

|  | L* | a* | b* |
|---|---|---|---|
| Control before treatment | 89 | 0 | 42 |
| + air sparging | 89 | −3 | 41 |
| + air sparging + laccase | 71 | 15 | 76 |

Example 4

Tea leaves (Broken Mixed Fannings, BMF, from Sri Lanka, 50 g/l) were boiled in 50 ml of water for 10 min. The mixture was allowed to cool to 50° C. and was treated with laccase from *Pleurotus ostreatus* at a final concentration of 37 mg/l, for 60 min under air sparging. Solid material was removed. Colour was measured at 0.2% soluble solids at pH=4 and the results are shown in table 4.

TABLE 4

|  | L* | a* | b* |
|---|---|---|---|
| Control before treatment | 77 | 13 | 88 |
| + air sparging | 74 | 16 | 89 |
| + air sparging + laccase | 38 | 40 | 63 |

Example 5

Homogenized tea leaves (dhool) (water:leaf=5:1) were treated with tannase (0.006% w/w on tea solids, Kikkoman) under exclusion of oxygen for 60 min at room temperature at an initial pH of 5.5. Subsequently oxygen was supplied and the solution was stirred for another 75 min. The colour of the solution darkened. After removal of the solid material, the solution was freeze-dried. This powder was dissolved in water (3% soluble solids) and was treated with laccase from *Pleurotus ostreatus* at a final concentration of 37 mg/l, for 60 min at 50° C. under air sparging (pH 6). Colour was measured after 60 min. and the results are shown in table 5.

TABLE 5

|  | L* | a* | b* |
|---|---|---|---|
| Colour of tannase-treated freeze-dried powder | 80 | 17 | 105 |
| + air sparging | 52 | 30 | 79 |
| + air sparging + laccase | 27 | 34 | 24 |

Example 6

Tannase used according to this example is Teazyme C (tradename of Quest International), a tannase enzyme formulation through fermentation of *Aspergillus niger* ssp. One unit of tannase is defined as the amount of enzyme which releases 1 micromole of gallic acid per minute when used on the filtered 0.5% black tea extract (substrate) at 50° C. and pH 5. The substrate is derived by extracting 0.5% of black tea (non reconditioned black tea of Brooke Bond India) in demineralised water for 20 minutes at 90° to 95° C. and filtering the same through Whatman No 42 filter paper.

Peroxidase used herein has been derived from Teazyme Lab (tradename of Quest International), 17,000 peroxidase units per g, an enzyme formulation wherin the peroxidase activity has been isolated and concentrated from soybean hulls.

The colour (CIE Lab) was measured using Illuminant C at an observation angle of 10° on Shimadzu PC 160 Plus using the colour software. The Haze value was measured in EBC (European Brewing Convention) units using Tannometer instrument of Pfeuffer GmbH, Germany.

200 ml (1.5% Instant Black tea solution) solution at pH 5 was pretreated with 18 tannase units at 50° C. for 60 minutes with stirring. This was followed by inactivation of tannase at 85° C. After cooling the pH of the solution was adjusted to 6 and the solution was divided in two aliquots of 100 ml each.

One of the 100 ml aliquots was treated with 0.012% Teazyme Lab (peroxidase) and 18 μl of hydrogen peroxide. This treatment was continued for 60 minutes at 40° C. with stirring, followed by inactivation of the enzyme at 85° C., cooling and adjusting the pH of the solution at 5. Subsequently the colour of the solution was measured at 0.3% tea solubles concentration and pH 5 after centrifugation at 5000 rpm for 10 minutes. The sample is referred to as 'Tannase & Peroxidase Treated' in table 6.

The control was run simultaneously with another 100 ml aliquot but without the treatment with peroxidase. In table 6 the colour value of this is referred to as 'Tannase Treated'.

TABLE 6

| Sample | L* | a* | b* | Haze EBC |
|---|---|---|---|---|
| Tannase Treated | 72.4 | 17.6 | 76.8 | 3.4 |
| Tannase & Peroxidase Treated | 58 | 28.8 | 83.3 | 4.6 |

A comparison of the observations shows that pretreatment with tannase followed by peroxidase treatment darkens the tea solution (decrease in L* value) an well as increases the redness (a*).

We claim:

1. A method of enhancing the color of black tea-based products, comprising treating black tea leaves or black tea extracts with a fungal laccase that has a redox potential higher than 550 mV in the presence of oxygen.

2. A method according to claim 1, wherein the laccase is derived from a Pleurotus species.

3. A method according to claim 1, wherein between 0.0001 and 2.5% of said laccase, on the basis of soluble tea solids, is used.

4. A method according to claim 3, wherein between 0.001 and 0.3% of said laccase, on the basis of soluble tea solids, is used.

5. A method according to claim 1, wherein the leaves or extracts are treated at a temperature between 20° and 65° C.

6. A method according to claim 1, wherein the leaves or extracts are treated at a pH between 3 and 8.

7. A method according to claim 6, wherein the pH is between 4 and 7.

8. A method according to claim 1, wherein the laccase is derived from *Pleurotus ostreatus*.

* * * * *